United States Patent [19]

Cloyd

[11] Patent Number: 5,203,767
[45] Date of Patent: Apr. 20, 1993

[54] LAPAROSCOPIC SURGICAL GAUZE AND THE LIKE

[76] Inventor: David W. Cloyd, 2540 Royal Crest, Escondido, Calif. 92025

[21] Appl. No.: 638,799

[22] Filed: Jan. 8, 1991

[51] Int. Cl.⁵ .............................................. A61F 13/20
[52] U.S. Cl. ....................................... 604/11; 604/15; 604/358; 604/362
[58] Field of Search ............... 604/362, 1, 11, 57, 604/904, 27, 28, 36, 48, 49, 286, 12–15, 16–18, 358; 606/191, 59; 128/749, 751, 756, 757, 759

[56] References Cited

U.S. PATENT DOCUMENTS

| | | | |
|---|---|---|---|
| 1,256,831 | 2/1918 | Rogers | 604/1 |
| 1,523,943 | 1/1925 | Fowle | 604/1 |
| 1,711,352 | 4/1929 | Jeffreys | 604/1 |
| 1,858,694 | 5/1932 | Walsh | 604/1 |
| 3,376,867 | 4/1968 | Kanbar et al. | 604/1 |
| 3,566,871 | 3/1971 | Richter et al. | 604/362 |
| 3,698,393 | 10/1972 | Stone | 604/362 |
| 3,837,344 | 9/1974 | Patience | 604/384 |
| 4,744,364 | 5/1988 | Kensey | 604/15 |
| 4,900,303 | 2/1990 | Lemelson | 604/11 |
| 5,061,274 | 10/1991 | Kensey | 604/15 |
| 5,074,840 | 12/1991 | Yoon | 604/11 |

Primary Examiner—Randall L. Green
Assistant Examiner—K. Reichle
Attorney, Agent, or Firm—Baker, Maxham, Jester & Meador

[57] ABSTRACT

A surgical gauze for use in combination with a trocar for laparoscopic surgery comprises a unitary body of surgical gauze of a size to fit through a trocar for use in surgical procedures, an elongated flexible radio-opaque tether of about 24 inches in length connected at one end to the body of gauze, and an anchoring device of a size too large for passage through a trocar connected to the other end of the tether.

20 Claims, 1 Drawing Sheet

LAPAROSCOPIC SURGICAL GAUZE AND THE LIKE

BACKGROUND OF THE INVENTION

The present invention relates to surgical tools and pertains particularly to an improved swab for use in laparoscopic surgery.

SUMMARY AND OBJECTS OF THE INVENTION

Recent development in surgical procedures and instruments enable gall bladder surgery to be carried out without making large openings into the body. One such procedure is referred to as laparoscopic cholecystectomy carried out through small keyhole size openings in the abdomen through which laparoscope and surgical instruments are inserted. In a preferred procedure, the abdominal cavity is inflated with air or $CO_2$ to provide working space. An elongated cannula or stainless steel tube, referred to as a trocar, is inserted through the abdominal wall into the stomach cavity. The trocar has a valve on the outer end to allow an instrument through and help maintain an air seal around instruments. The surgical procedures are carried out by means of instruments inserted through the tube or tubes.

This surgical procedure, however, does not allow certain surgical tools to be used. One such tool that cannot be readily used in the traditional manner is the surgical peanut. The surgical peanut is a body of surgical gauze having the form of a peanut that is widely used by means of forceps to strip away certain flesh from organs and the like without the use of a scalpel. Such peanuts and other similar articles are difficult to use because of the danger of loss of the article within the surgical cavity.

I have devised means for enabling the use of surgical peanuts and the like without the danger of loss and the like.

SUMMARY AND OBJECTS OF THE INVENTION

It is the primary object of the present invention to provide an improved laparoscopic surgical tool.

In accordance with a primary aspect of the present invention, a surgical gauze is provided with an elongated umbilical cord with an anchor on an outer end thereof that prevents it being pulled through a trocar.

BRIEF DESCRIPTION OF THE DRAWING

The above and other objects and advantages of the present invention will become apparent from the following description when read in conjunction with the accompanying drawings wherein.

DETAILED DESCRIPTION OF A PREFERRED EMBODIMENT

Figure 1:
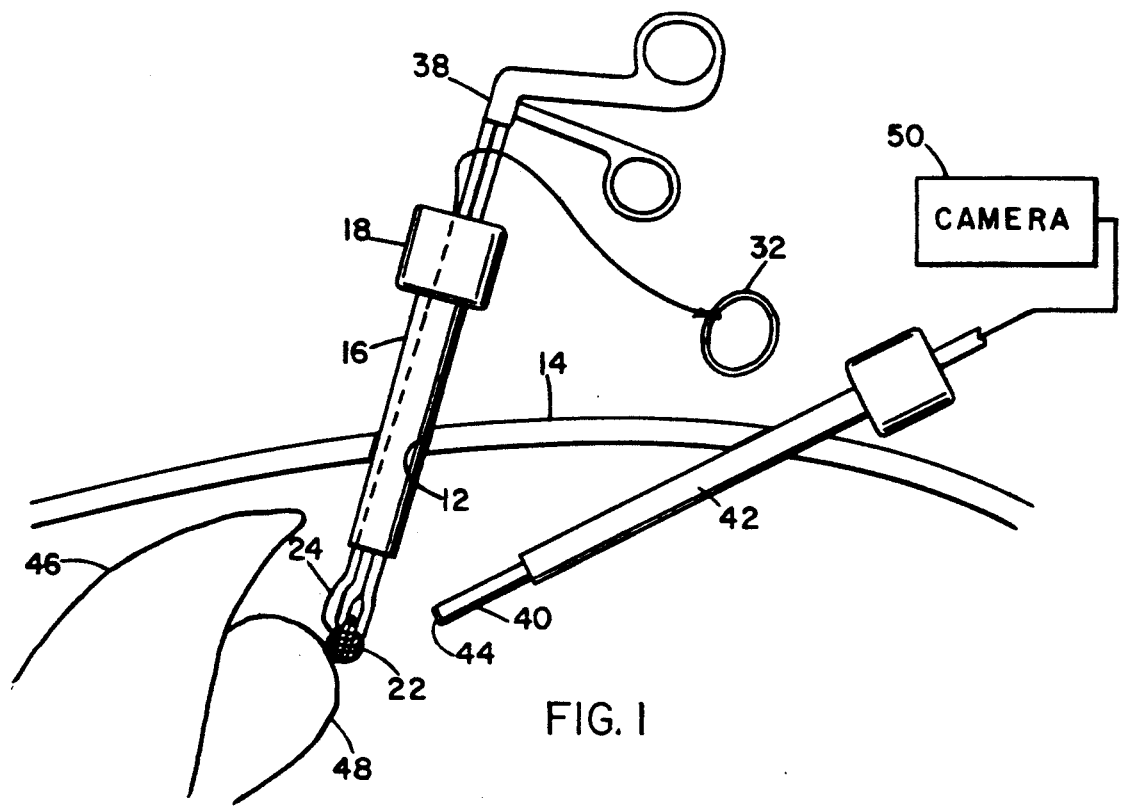
FIG. 1 is a diagrammatic illustration of a preferred embodiment of the invention in use.

Referring to the drawing, and particularly to FIG. 1, there is illustrated an example of laparoscopic surgery being carried out on a gallbladder. In this procedure, one or more small incisions or holes 12 is made in the wall 14 of a patient's abdomen. A stainless steel tube or trocar 16 is inserted through the opening 12, and appropriately designed instruments are passed through the tube for carrying out the procedure. A trocar is an elongated, hollow tube of approximately 10 to 12" in length with a bore of approximately ½" in diameter through which instruments are inserted for operation inside the abdominal cavity. The trocar 16 has a valve 18 on the outer end thereof for enabling the passage of an instrument 38, and to control or prevent the passage of gas from the abdominal cavity.

A laparoscope 40 is provided and inserted through a second trocar 42 to provide means for viewing the surgical site. The laparoscope 40 is provided with a source of light and an electronic eye or camera lens at the forward or inner end 44, which receives and transmits an image of the internal organs or the like via a video camera or the like 50 onto a video screen (not shown). The surgeon is able to see and manipulate scalpels, forceps and the like in the abdominal cavity through one or more of the trocars by means of this visual aid. For example, he is able to view the gripping jaws of a gripper or forceps 38 grasping and manipulating a surgical peanut 22 against a gall bladder 48 located below a liver 46 in an abdominal cavity, as illustrated.

One difficulty with this approach, however, is that it is difficult to utilize many of the handy surgical tools normally available to the surgeon. The small access opening of the trocar limits and sometimes prohibits the use of many conventional tools, such as swabs, sponges, surgical peanuts and the like. One very useful tool, normally used by the surgeon for stripping away flesh and the like, is known as a surgical peanut. This is a one-by-one centimeter tightly wrapped gauze, wrapped in the form of a ball or the like which resembles a peanut. These are normally grasped in the jaws of forceps or other grasping tool 38 and are used for blunt dissection during intra-abdominal procedures.

With the laparoscopic approach to surgery, however, it is difficult to pass these and other similar gauzes and the like through the trocar and retrieve them without the danger of losing them. For this reason, the use of peanuts and other small surgical gauzes is avoided.

Figure 2:
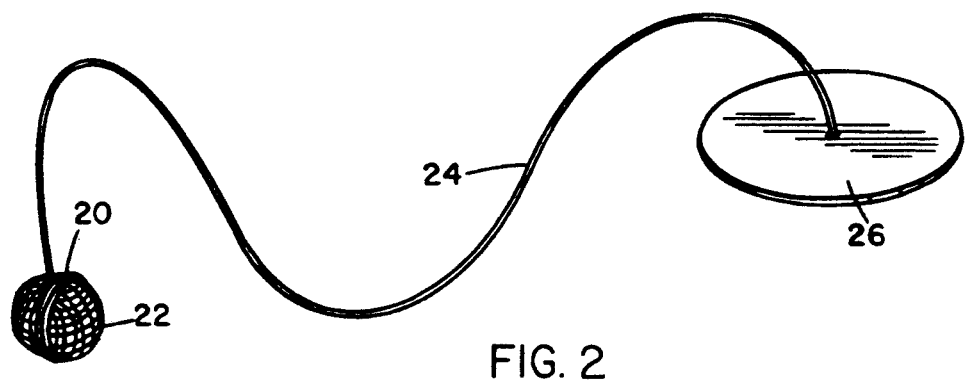
FIG. 2 is a perspective view of a preferred embodiment of the invention.

Referring to FIG. 2 of the drawing, applicant's invention comprises a gauze peanut 22 of a typical construction, having a radio-opaque marker 20 imposed thereon, to which is attached an elongated tether or umbilical 24 of on the order of about 24", and a suitable anchoring means 26, such as a plastic disc or ring on the order of approximately 25 mm. in diameter by about 1 mm. in thickness. The umbilical cord is preferably of a suitable braided polytetrafluroethylene available under the trademark TEFLON from the Du Pont Company or the equivalent thereof and should be radio-opaque. This can be passed through the trocar as illustrated in FIG. 1, with the gauze grasped in forceps, with the tether extending along the trocar and prevented from passing therethrough by means of the anchoring disc 26, which could also use a ring 32 instead of the disc 26. This conveniently anchors the peanut so that it cannot be lost during surgery. Once the use of the peanut is concluded, it may be easily retrieved from its tethered position within the abdominal cavity.

Figure 3:
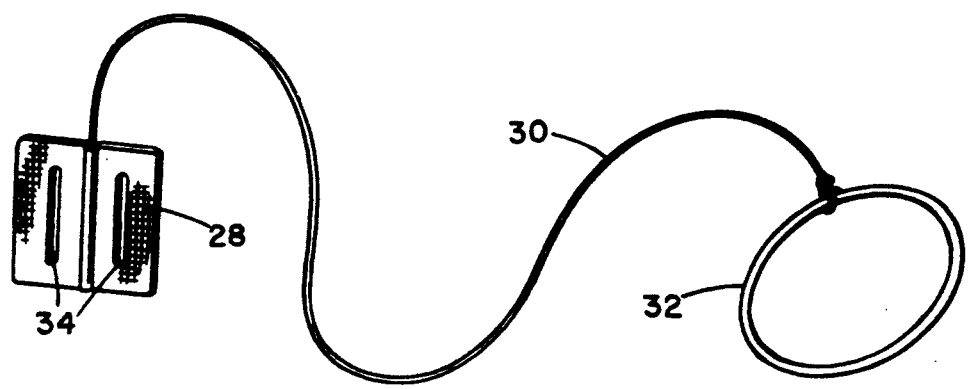
FIG. 3 is a perspective view of an alternate embodiment of the invention.

Other similar surgical instruments may also be fashioned and used in this manner. For example, referring to FIG. 3, a small sponge or gauze 28, typically called a cottonoid, is similarly prepared for use in laparoscopic surgery. As illustrated in FIG. 3, a laparoscopic sponge of the type typically referred to as a cottonoid 28 is attached to one end of an elongated radio-opaque tether 30 which has, on the opposite end, an anchoring disc or ring 32. The cottonoid also is preferably provided with one or more radio-opaque markers 34 so that it may be located by x-ray within the abdominal cavity.

Thus, the present invention provides method and apparatus which enable the use of a number of surgical tools not otherwise available to the surgeon through the laparoscopic procedures.

In operation, a surgical peanut or cottonoid gauze having an elongated umbilical cord or tether, as illustrated, is selected. The gauze grasped in forceps and passed through the trocar is manipulated in the abdominal or other body cavity in the usual manner, as illustrated in FIG. 1. The umbilical cord extending to the exterior of the abdominal cavity through the trocar, with the anchoring disc preventing its passage through the trocar, ensures that the surgical tool will not be lost.

While I have illustrated and described my invention by means of specific embodiments, it is to be understood that numerous changes and modifications may be made therein without departing from the spirit and scope of the invention as defined in the intended claims. Applicant sincerely believes that the foregoing description and the accompanying drawings clearly and fully illustrate the invention in a manner and to enable one of ordinary skill in the art to carry out the invention. Moreover, applicant sincerely believes that the foregoing illustration represents the best mode for carrying out the invention known to him.

I claim:

1. A surgical tool for use in laparoscopic surgery comprising:
    a surgical gauze formed of a unitary body of a size to fit through a trocar for use in laparoscopic surgical procedures;
    an elongated flexible tether connected at one end to said body; and
    an article of a size to prevent its passage through a trocar connected to the other end of said tether.

2. A surgical tool according to claim 1 wherein said body is a surgical peanut.

3. A surgical tool according to claim 1 wherein said body is a surgical sponge.

4. A surgical tool according to claim 1 wherein said article is a disc.

5. A surgical tool according to claim 4 wherein said body is a surgical peanut.

6. A surgical tool according to claim 4 wherein said body is a surgical sponge.

7. A surgical tool according to claim 1 wherein said flexible tether is a radio-opaque polytetrafluroethylene cord o order of about twenty-four inches in length.

8. A surgical gauze for use in combination with a trocar for laparoscopic surgery comprising: a unitary body of surgical gauze of a size to fit through a trocar for use in laparoscopic surgical procedures; an elongated flexible tether of about 24 inches in length connected at one end to said body of gauze; and an anchoring device of a size too large for passage through a trocar connected to the other end of said tether.

9. A surgical tool according to claim 8 wherein said body is a surgical peanut.

10. A surgical tool according to claim 9 wherein said anchoring device is a disc.

11. A surgical tool according to claim 9 wherein said anchoring device is a ring.

12. A surgical tool according to claim 9 wherein said flexible tether is a radio-opaque polytetrafluroethylene cord.

13. A surgical tool according to claim 8 wherein said body is a surgical sponge.

14. A surgical tool according to claim 13 wherein said anchoring device is a ring.

15. A method of use of surgical gauzes during laparoscopy surgery in a body cavity comprising the steps of:
    selecting and inserting a trocar through an opening into an abdominal body cavity for providing access therethrough to a surgical site within said body cavity;
    selecting a surgical gauze of a size to pass through said trocar;
    providing said gauze with an elongated flexible radio-opaque tether of a length to extend through said trocar and be manipulated within said body cavity;
    providing an outer end of said tether with an anchoring device for preventing its passing through the trocar;
    selecting grasping means sized to fit through said trocar for grasping said gauze; and
    grasping said surgical gauze with said grasping means and extending said gauze through said trocar into said body cavity.

16. A method of use of surgical gauzes according to claim 15 wherein said step of selecting a surgical gauze comprises selecting a surgical peanut.

17. A method of use of surgical gauzes according to claim 16 wherein said step of providing an outer end of said tether with an anchoring device comprises providing said tether with a circular disc.

18. A method of use of surgical gauzes according to claim 16 wherein said step of providing an outer end of said tether with an anchoring device comprises providing said tether with a circular ring.

19. A method of use of surgical gauzes according to claim 15 wherein said step of selecting a surgical gauze comprises selecting a surgical sponge.

20. A method of use of surgical gauzes according to claim 19 wherein said step of providing an outer end of said tether with an anchoring device comprises providing said tether with a circular disc.

* * * * *